United States Patent
Tsuda (10) Patent No.: US 10,545,249 B2
(45) Date of Patent: Jan. 28, 2020

(54) RADIATION DETECTION DEVICE

(71) Applicant: Shimadzu Corporation, Kyoto (JP)

(72) Inventor: Tomoaki Tsuda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/703,287

(22) Filed: Sep. 13, 2017

(65) Prior Publication Data

US 2018/0156928 A1 Jun. 7, 2018

(30) Foreign Application Priority Data

Dec. 2, 2016 (JP) .................................. 2016-234825

(51) Int. Cl.
| | |
|---|---|
| *G01T 1/16* | (2006.01) |
| *G01T 1/24* | (2006.01) |
| *A61B 6/03* | (2006.01) |
| *G01T 1/36* | (2006.01) |
| *G01T 1/29* | (2006.01) |

(52) U.S. Cl.
CPC .............. *G01T 1/248* (2013.01); *A61B 6/037* (2013.01); *G01T 1/249* (2013.01); *G01T 1/2985* (2013.01); *G01T 1/362* (2013.01)

(58) Field of Classification Search
CPC ........... G01T 1/2018; G01T 1/20; G01T 1/24; H01L 27/14663; H04N 5/32
See application file for complete search history.

(56) References Cited

U.S. PATENT DOCUMENTS

| | | | | |
|---|---|---|---|---|
| 5,677,536 | A * | 10/1997 | Vickers | .................. G01T 1/1642 250/252.1 |
| 8,294,110 | B2 | 10/2012 | Burr | |
| 2005/0040334 | A1* | 2/2005 | Beyerle | ................... G01T 1/365 250/339.07 |
| 2006/0029183 | A1* | 2/2006 | Borghese | ................ G06T 5/008 378/62 |
| 2013/0077848 | A1* | 3/2013 | Yamada | ................. G01T 1/1644 382/131 |

FOREIGN PATENT DOCUMENTS

JP 2012-189583 A 10/2012

OTHER PUBLICATIONS

Hamamatsu Photonics K.K., Opto-Semiconductor Handbook Chapter 03 Si APD, MPPC, (online), available from<https://www.hamamatsu.com/jp/a/hamamatsu/overview/bsd/solid_state_division/related_documents.html>.

* cited by examiner

*Primary Examiner* — David P Porta
*Assistant Examiner* — Mamadou Faye
(74) *Attorney, Agent, or Firm* — Maier & Maier, PLLC (57) ABSTRACT

A radiation detection device includes a scintillator group which includes a plurality of scintillators; an optical detection unit which is provided in each scintillator and detects scintillation light; and a control unit which corrects a detection signal based on a value of energy of a radiation and a plurality of features included in a histogram based on the acquired detection signal.

5 Claims, 9 Drawing Sheets

RADIATION DETECTION DEVICE

CROSS-REFERENCE TO RELATED APPLICATIONS

The priority application number JP 2016-234825, radiation detection device, Dec. 2, 2016, Tomoaki Tsuda, upon which this patent application is based are hereby incorporated by reference.

BACKGROUND OF THE INVENTION

Field of the Invention

The present invention relates to a radiation detection device and more particularly to a radiation detection device including a scintillator.

Description of Related Art

Hitherto, a radiation detection device including a scintillator is known. Such a radiation detection device is disclosed in, for example, JP-A-2012-189583.

JP-A-2012-189583 discloses a positron emission tomographic imaging device (a radiation detection device) including a scintillator array which includes a plurality of scintillators, a plurality of optical detection units which detect scintillation light generated when a gamma ray is incident to the scintillator, and a light guide which diffuses the scintillation light (fluorescence) so that the scintillation light is incident to one or the plurality of optical detection units.

However, in the positron emission tomographic imaging device (the radiation detection device) disclosed in JP-A-2012-189583, a variation in optical path length occurs in the diffused scintillation light due to the diffusion by the light guide and thus the time to reach the light detection unit varies. For this reason, there is a problem in which the gamma ray incidence time cannot be accurately acquired. Further, since only a total signal value can be obtained from signal values detected by the plurality of optical detection units, it is difficult to acquire the degree of saturation of how much each of the optical detection units has caused detection omission due to saturation. For that reason, there is a problem in which the energy acquired by each optical detection unit is not corrected with high accuracy only from the total value obtained by adding the values. Further, the scintillator (position) to which the gamma ray is incident is estimated based on the distribution of the energy of the scintillation light in the plurality of optical detection units. However, the distribution of the energy of the scintillation light in the optical detection units is dependent on a distance (positional relation) between the scintillator and the optical detection unit, but since the incidence position is estimated by the reverse ratio (center position) of the energy acquired by each optical detection unit without considering the effect of the distance, it is difficult to mention that an accurate position can be acquired. In addition, since the incidence position is estimated based on the energy of which the saturation degree is not corrected with high accuracy, a problem arises in that the scintillator (position) to which the gamma ray is incident is not easily specified. Further, there is a problem in which the gamma ray incidence time is not easily acquired with high accuracy due to the uncertain gamma ray incidence position. From these results, there is a problem in which the gamma ray incidence time, the gamma ray incidence position, and the energy caused by the gamma ray are not easily acquired with high accuracy.

SUMMARY OF THE INVENTION

The invention has been made to solve the above-described problems and an object of the invention is to provide a radiation detection device capable of accurately acquiring a gamma ray incidence time, a gamma ray incidence time position, and energy generated by a gamma ray.

In order to attain the above-described object, a radiation detection device of one aspect of the invention includes: a scintillator group which includes a plurality of scintillators emitting a plurality of scintillation lights on the basis of receiving of a radiation having a predetermined energy amount; a plurality of optical detection units which include a plurality of photoelectric conversion elements outputting detection signals on the basis of incidence of the scintillation light; and a control unit which acquires the detection signals output from the optical detection units, wherein the optical detection unit is provided in each scintillator to detect the scintillation light generated from one scintillator, and wherein the control unit is configured to correct the detection signals on the basis of a plurality of features included in a histogram based on the acquired detection signals and a value of the energy of the radiation.

In the radiation detection device according to one aspect, as described above, the optical detection unit is provided in each scintillator to detect the scintillation light generated from one scintillator. Further, the control unit is configured to correct the detection signal based on a plurality of features included in the histogram based on the acquired detection signal. Accordingly, since the optical detection unit detects the scintillation light generated from one scintillator, it is possible to accurately specify a certain scintillator to which the gamma ray is incident. Further, since the scintillation light is made to be incident to one optical detection unit, a variation in the path of the scintillation light is suppressed and thus the gamma ray incidence time can be acquired with high accuracy. Further, since the detection signal is corrected on the basis of a plurality of features included in the histogram based on the acquired detection signal and the value of the energy of the radiation, the detection omission due to the saturation can be corrected and thus the read value (the energy) of the detection signal can be corrected with high accuracy. As a result, the gamma ray incidence time, the gamma ray incidence position, and the energy generated by the gamma ray incidence can be acquired with high accuracy. Particularly, in the case of an application to a TOF (Time of Flight) positron emission tomography apparatus which acquires a position where the pair annihilation of electrons and positrons occurs on the paths of two gamma rays from a difference in detection time of two gamma rays generated by the pair annihilation of electrons and positrons, the gamma ray incidence time and the gamma ray incidence position can be acquired with high accuracy. Accordingly, it is possible to highly accurately acquire a position where the pair annihilation of electrons and positrons occurs.

In the radiation detection device according to one aspect, desirably, the control unit is configured to acquire a correlation between a detection value of the optical detection unit and a correction value of the detection value for correcting the detection signal based on a photoelectric absorption peak read value and a compton edge read value which are the features included in the histogram. According to such a configuration, since the correlation between the detection value of the optical detection unit and the correction value of the detection value for correcting the detection signal can be acquired only from the photoelectric absorption peak read value and the compton edge read value corresponding to the radiation having predetermined energy, information necessary for the correction can be simply acquired. In addition, the photoelectric absorption peak indicates a peak of an output signal value when the total energy of the incident gamma ray is converted into the scintillation light and is detected in one scintillator. Further, the compton edge indicates an edge of an output signal value corresponding to the maximum energy given to electrons when the incident gamma ray collides with electrons inside the scintillator to be flipped (rebounded).

In this case, desirably, the control unit acquires the correlation based on a quadratic function in which a theoretical value corresponding to the correction value is correlated with the photoelectric absorption peak read value and the compton edge read value included in the histogram. According to such a configuration, since the correlation for correcting the read value can be determined by the quadratic function, the correlation can be acquired by a simple and easy process. Specifically, it is possible to simply and easily determine the shape of the quadratic function corresponding to the correlation by the use of three points including an origin (in which a corrected value is zero when the read value is zero), a point representing the photoelectric absorption peak (which is predetermined total energy of the incident gamma ray corresponding to the corrected value for the photoelectric absorption peak read value), and a point representing the compton edge (which is ⅔ of predetermined total energy of the incident gamma ray corresponding to the corrected value for the compton edge read value) and determined from the theoretical value corresponding to the read value and the correction value.

In the radiation detection device which acquires the correlation for correcting the detection signal on the basis of the photoelectric absorption peak read value and the compton edge read value, desirably, the control unit is configured to correct the vicinity of the photoelectric absorption peak included in the histogram of the scintillation light on the basis of the acquired detection signal. According to such a configuration, since the shape of the photoelectric absorption peak can be accurately corrected, it is possible to highly accurately acquire the full width at half maximum representing a variation in the photoelectric absorption peak. As a result, it is possible to accurately estimate an error in calculation using the gamma ray incidence time, the gamma ray incidence position, and the energy obtained by measurement. Particularly, in the case of the application to the TOF positron emission tomography apparatus, it is possible to inhibit an excessive correction or insufficient correction when a diagnosis image formed by measurement data is corrected.

In the radiation detection device according to one aspect, the radiation detection device is desirably used in a positron emission tomography apparatus. According to such a configuration, it is possible to more accurately detect the incidence time of the gamma ray emitted by the pair annihilation of electrons and positrons.

DESCRIPTION OF THE PREFERRED EMBODIMENT(S)

Hereinafter, detailed embodiments of the invention will be described with reference to the drawings.

(Overall Configuration of Radiation Detection Device)

First, an overall configuration of a radiation detection device 100 according to the embodiment will be described with reference to FIG. 1. In the embodiment, an example in which the radiation detection device 100 is used in a TOF positron emission tomography apparatus (hereinafter, referred to as a TOF-PET apparatus) 101 will be described. In addition, the TOF positron emission tomography apparatus is an example of a "positron emission tomography apparatus" of claims.

Figure 1:
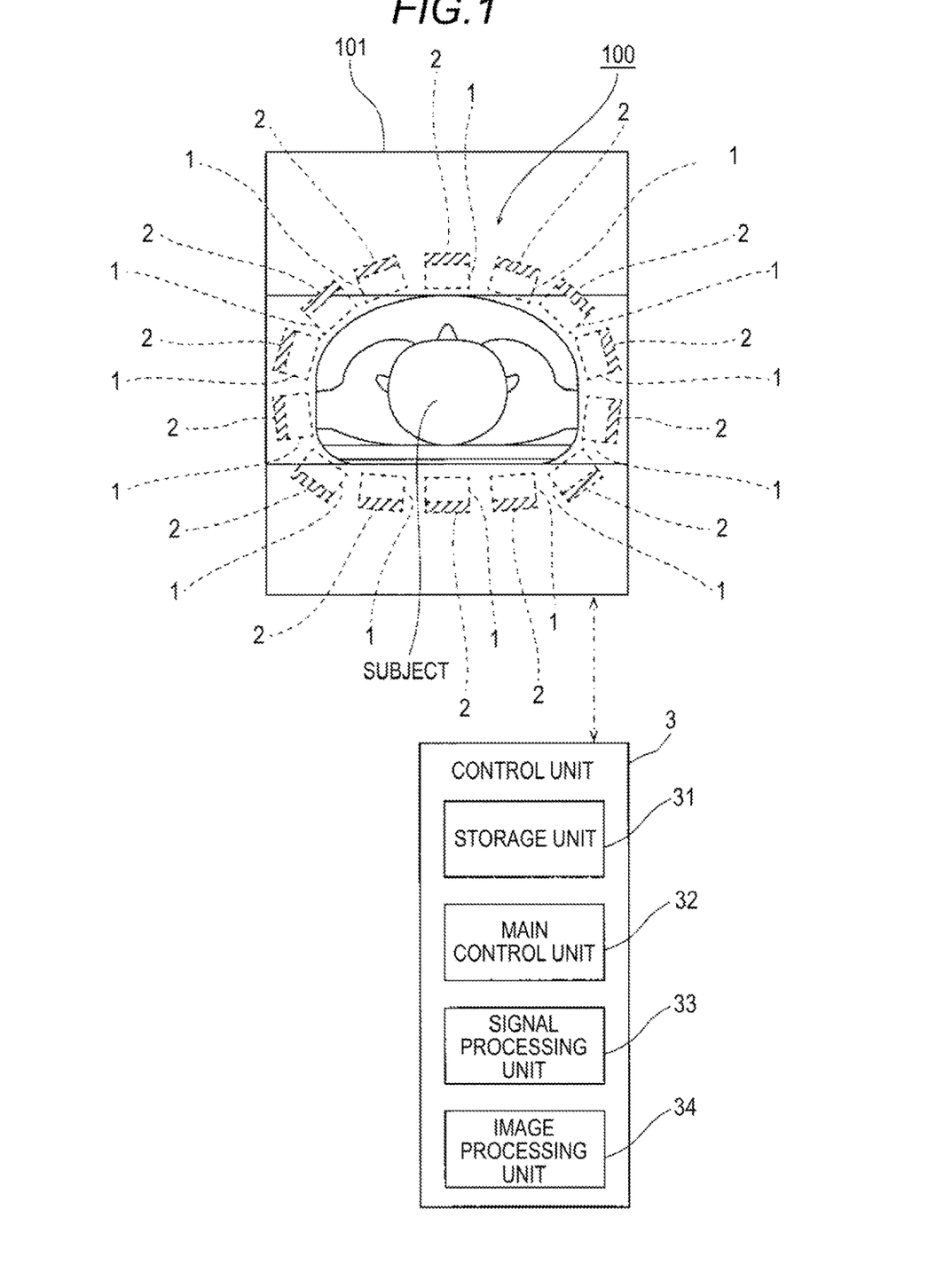
FIG. 1 is a block diagram showing a radiation detection device according to one embodiment of the invention.

As shown in FIG. 1, the TOF-PET apparatus 101 is an apparatus which captures an image inside a subject (a human body or the like) using a drug labeled with a positron emitting nuclide. Specifically, the TOF-PET apparatus 101 is configured to acquire a position where pair annihilation occurs by detecting a pair of gamma rays (radiations) generated by the pair annihilation of positrons and electrons caused by the drug. Then, the TOF-PET apparatus 101 is configured to form (capture) an image inside a subject by acquiring a plurality of positions where the pair annihilation of the drug occurs. Then, the formed image is used in image diagnosis for determining whether cancer cells exist.

Further, the radiation detection device 100 used in the TOF-PET apparatus 101 is configured to capture a subject in a supine position. Specifically, the radiation detection device 100 is disposed at a plurality of positions to surround the subject while an optical detection unit 2 to be described later is aligned to a body axis (an axis extending from a head portion to a leg portion) of the subject. Further, the radiation detection device 100 is also disposed at a plurality of positions to have the same configuration in a direction in which the body axis of the subject (not shown) extends (a direction extending to the back of the page). Here, the gamma ray generated by the pair annihilation of the drug is the radiation of 511 keV and cannot be directly detected by the optical detection unit 2. Here, a scintillator group 1 is provided between the subject and the radiation detection device 100. Accordingly, when the gamma ray is incident to the scintillator group 1, a phosphor inside the scintillator group 1 emits light by the gamma ray so that scintillation light (fluorescence) is generated. Then, the radiation detection device 100 is configured to detect the scintillation light generated by the gamma ray.

Unlike a general PET apparatus (a positron emission tomography apparatus) that acquires only the incident direction of the gamma ray, the TOF-PET apparatus 101 is configured to acquire a position where the pair annihilation of positrons and electrons occurs within a range of lines of about several tens of cm by acquiring a slight difference in incidence time of the pair of gamma rays caused by the pair annihilation of positrons and electrons. The gamma ray moving at the speed of light travels a few cm to several tens of cm just in a few hundred picoseconds. For that reason, it is an essential requirement to accurately acquire the incidence time in order to accurately acquire a position where the gamma ray is generated.

Next, a configuration of the radiation detection device 100 according to the embodiment of the invention will be described with reference to FIGS. 1 and 2.

As shown in FIG. 1, the radiation detection device 100 according to the embodiment of the invention includes the scintillator group 1, the optical detection unit 2, and a control unit 3.

The radiation detection device 100 includes the scintillator group 1 which includes a plurality of scintillators 10 emitting a plurality of scintillation lights based on the receiving of the radiation having a predetermined energy amount. As shown in FIG. 1, the scintillator group 1 is a group of a block of the plurality of scintillators. Further, as shown in FIGS. 2A and 2B, the block of the scintillator includes, for example, a group of the scintillators 10 arranged by nine rows and ten columns.

The scintillator 10 generates the scintillation light corresponding to the energy received from the gamma ray in response to the gamma ray incident thereinto. The scintillation light corresponds to, for example, 10000 or more photons when absorbing the gamma ray of 511 keV. Further, a reflection material is provided between the scintillators 10 and the scintillation light which is generated by the scintillator 10 does not leak to the outside of the scintillator 10. For that reason, the scintillation light which is generated by one scintillator 10 is detected by the corresponding one optical detection unit 2. However, there is a case where the gamma ray may pass through the reflection material and enter into another scintillator 10. In addition, it is desirable that the scintillator 10 be formed as a Lu-type inorganic scintillator that is highly sensitive and excellent in response at high speed. Specifically, the scintillator 10 is formed of, for example, crystals of LSO ($Lu_2SiO_5$), LYSO ($Lu_{2-x}Y_xSiO_5$) LGSO ($Lu_{2-x}Gd_xSiO_5$), LuAG ($Lu_3Al_5O_{12}$), LFS (Lutetium Fine Silicate), or the like.

Further, the radiation detection device 100 includes the optical detection units 2 which include a plurality of photoelectric conversion elements (pixels) 21 (see FIG. 2C) outputting detection signals based on the incidence of the scintillation light. The optical detection unit 2 is configured as, for example, a SiPM (Silicon Photomultipliers). The photoelectric conversion element 21 includes, for example, an avalanche photodiode (APD) and a quenching resistor. The avalanche photodiode is a photodiode to which a large voltage equal to or higher than a breakdown voltage is applied to a reverse bias and normally no current flows thereto. Since a large current flows from the avalanche photodiode when photons are incident thereto, a detection signal having a good S/N ratio per unit photon can be output. Further, since the quenching resistor is connected in series to the avalanche photodiode and a voltage is applied due to a current flowing from the avalanche photodiode, the voltage applied to the avalanche photodiode falls to be lower than a breakdown voltage. Accordingly, a current flowing to the avalanche photodiode is stopped so that photons can be detected again.

Further, the radiation detection device 100 includes the control unit 3 which acquires a detection signal output from the optical detection unit. The control unit 3 includes a storage unit 31, a main control unit 32, a signal processing unit 33, and an image processing unit 34. Further, the control unit 3 includes an information processing device such as a personal computer (PC).

The storage unit 31 includes a hard disk drive (HDD) and a memory. Further, the storage unit 31 stores various programs which are executed by the main control unit 32 or the signal processing unit 33, captured image data, or various data including a measurement value and a theoretical value of a predetermined gamma ray necessary for a signal correction to be described later.

The main control unit 32 includes a CPU (Central Processing Unit) and the like. Further, the main control unit 32 allows the PC to serve as the control unit 3 of the radiation detection device 100 and the TOF-PET apparatus 101 by executing a control program stored in the storage unit 31. Further, the main control unit 32 performs a control of the TOF-PET apparatus 101 (for example, a movement of a bed on which a subject lies).

The signal processing unit 33 performs a correction process on the data of the detection signal output value (corresponding to a detection value or a pixel value) of the photoelectric conversion element (pixel) 21 output from the optical detection unit 2. The detection signal correction process will be described later in detail.

The image processing unit 34 creates a radiation captured image based on the detection signal and the correction detection signal output from the signal processing unit 33. The scintillation lights which are generated by the incidence of two gamma rays emitted in the opposite directions of substantially 180° due to the pair annihilation are detected by two facing optical detection units 2 substantially at the same time. Thus, it is understood that the gamma rays are generated at several positions on the paths of two facing optical detection units 2 and are incident to the optical detection units. Since a time resolution is not sufficient in the general PET apparatus, it is difficult to know a position where the pair annihilation occurs on the path. For that reason, an image is displayed such that a plurality of radiation paths are collected and a path overlapping area is set as a gamma ray generation source. In the TOF-PET apparatus 101, a difference in incidence time of two gamma rays is acquired and is specified as a line having a range (considering the width of the measurement error). Then, an image is displayed such that a line overlapping area is set as a gamma ray generation source. For that reason, it is possible to more accurately obtain position information of the organ or the brain of the subject.

In addition, the signal processing unit 33 and the image processing unit 34 may be respectively calculation processing units respectively dedicated for the signal process and the image process or a CPU may serve as the signal processing unit 33 and the image processing unit 34 by allowing the CPU to execute a signal process program and an image process program. Further, devices which are dedicated for the signal process or the image process may be provided as the signal processing unit 33 and the image processing unit 34. The signal processing unit 33 and the image processing unit 34 may be integrated with each other.

(Correction of Detection Signal)

Next, a correction process for the detection signal of the radiation detection device will be described with reference to FIGS. 3 to 9.

The photoelectric conversion element (pixel) 21 included in the optical detection unit 2 detects photons of the scintillation light incident to the position of the photoelectric conversion element 21 and outputs a detection signal. The detection signal reflecting the number of photons and output from the plurality of photoelectric conversion elements 21 is represented as energy information of the scintillation light based on the gamma ray incident to the scintillator 10. Further, it is also possible to acquire the gamma ray incidence time and the flight time from the generation of the gamma ray to the incidence calculated therefrom from the time of acquiring the signal. However, in a configuration in which all these information items are acquired by each photoelectric conversion element 21, the configuration of the apparatus increases in size and the detection signal data processing burden increases. For this reason, the detection signal for the energy value is output as a signal grouped for each block of the scintillator 10 and is acquired by the control unit 3. Further, the detection position signal is output from each optical detection unit 2 so that the detected scintillator is individually distinguished and is acquired by the control unit 3.

The photoelectric conversion element 21 needs a recovery time (for example, several tens to several hundreds nsec) until another photon can be detected after the detection of one photon. Further, only one photon can be detected by one photoelectric conversion element 21 at one time. For that reason, when many photons are incident to the same position in a short time, photons may not be detected. Since the detection omission of photons easily occurs as the number of photons of the scintillation light increases, the linearity of the detection signal becomes poor as the number of photons of the scintillation light becomes close to the total number of the photoelectric conversion elements (pixels) 21 connected to the scintillator 10. Specifically, when the number of photons of the generated scintillation light is smaller than the total number of the photoelectric conversion elements 21, a linear relation between the number of photons of the scintillation light and the output value of the detection signal is established. However, as the number of photons of the generated scintillation light becomes close to the total number of the photoelectric conversion elements 21, the detection signal increase rate falls (see FIG. 6).

Here, the detection efficiency of the optical detection unit 2 is improved in order to obtain the radiation detection device 100 having a high time resolution. Specifically, a light receiving area for each photoelectric conversion element 21 is increased in order to decrease a dead space existing between the photoelectric conversion elements 21. Accordingly, the number of the photoelectric conversion elements (pixels) included in the optical detection unit 2 is small. Further, the scintillator 10 is densely divided with respect to the gamma ray incidence surface in order to obtain the radiation detection device 100 having a high space resolution. Accordingly, since an area occupied by one optical detection unit 2 decreases, the number of the photoelectric conversion elements (pixels) included in the optical detection unit 2 also decreases.

As described above, the radiation detection device 100 having a high time resolution and a high space resolution and used in the TOF-PET apparatus 101 has a tendency that the number of the photoelectric conversion elements (pixels) 21 for one scintillator 10 is not sufficient. For that reason, there is a case in which the detection signal output from the optical detection unit 2 may not keep linearity. When the linearity of the output value of the detection signal is poor, correct information cannot be obtained as in the full width at half maximum of the photoelectric conversion scattering peak to be described later. Thus, there is a need to acquire a correct output value reflecting linearity by correcting the detection signal.

Here, in the embodiment, the control unit 3 is configured to correct the detection signal on the basis of a plurality of features included in the histogram based on the acquired detection signal and the value of the energy of the predetermined radiation.

Further, the control unit 3 is configured to acquire a correlation between the detection value of the optical detection unit 2 and the correction value of the detection value for correcting the detection signal based on the photoelectric absorption peak read value and the compton edge read value corresponding to the features included in the histogram.

Further, the correlation is acquired on the basis of a quadratic function in which a theoretical value corresponding to the correction value is correlated with the photoelectric absorption peak read value and the compton edge read value included in the histogram.

Further, the control unit 3 is configured to correct the vicinity of the photoelectric absorption peak included in the histogram of the scintillation light on the basis of the acquired detection signal.

Figure 3A:
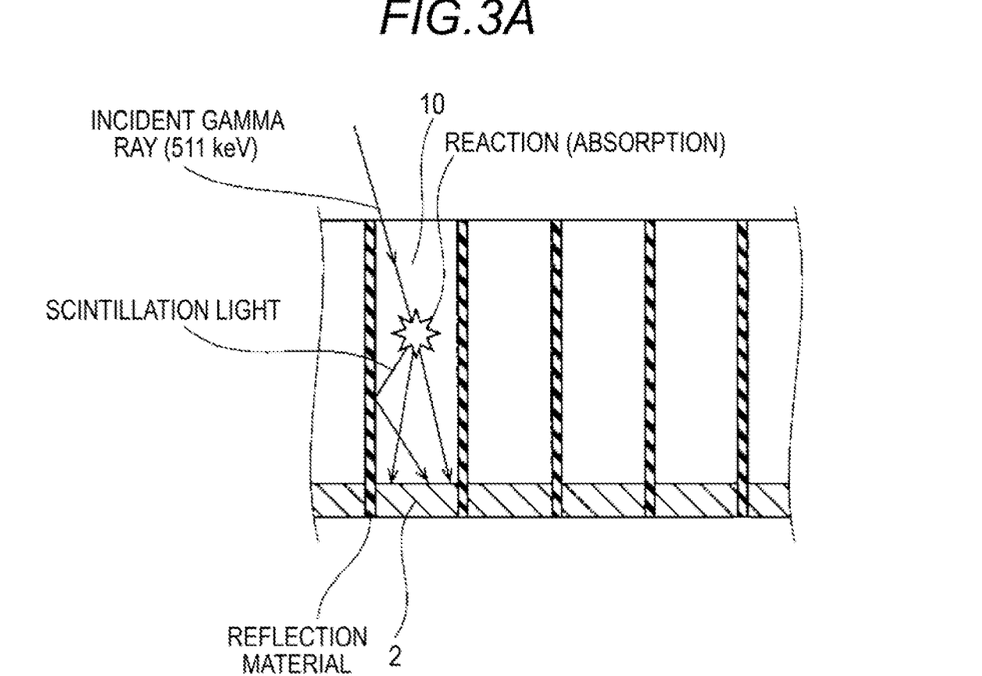
FIG. 3A is a diagram showing a state where scintillation light is generated when a gamma ray is incident to the scintillator of the radiation detection device according to one embodiment of the invention.

Specifically, the value of the detection signal is corrected by the given energy value of the predetermined gamma ray incident to the scintillator 10. It is understood that each of two gamma rays generated by a drug reaction (the pair annihilation of electrons and positrons) has energy of 511 keV. For that reason, when all gamma rays incident to one certain scintillator 10 cause a reaction inside the scintillator 10 as shown in FIG. 3A, the scintillation light of the energy corresponding to 511 keV is generated. Since the scintillators 10 are divided by the reflection material, the scintillation light generated inside the scintillator 10 does not enter other scintillators 10. For this reason, the scintillation light is detected by one optical detection unit 2 (the photoelectric conversion element 21) connected to one scintillator 10 to which the gamma ray is incident. In this way, an event in which the scintillation light corresponding to the total energy of the incident gamma ray is detected will be referred to as a photoelectric absorption event.

The scintillation light having the gamma ray of 511 keV includes, for example, ten thousands or more photons. Since photons may be absorbed into the scintillator or the reflection material, all photons do not reach the photoelectric conversion element 21, but may be similar to the number of the photoelectric conversion elements 21 (for example, thousands to tens of thousands). As a result, there is a case in which photons are successively incident to the same photoelectric conversion element 21 so that detection omission is caused by saturation.

Figure 3B:
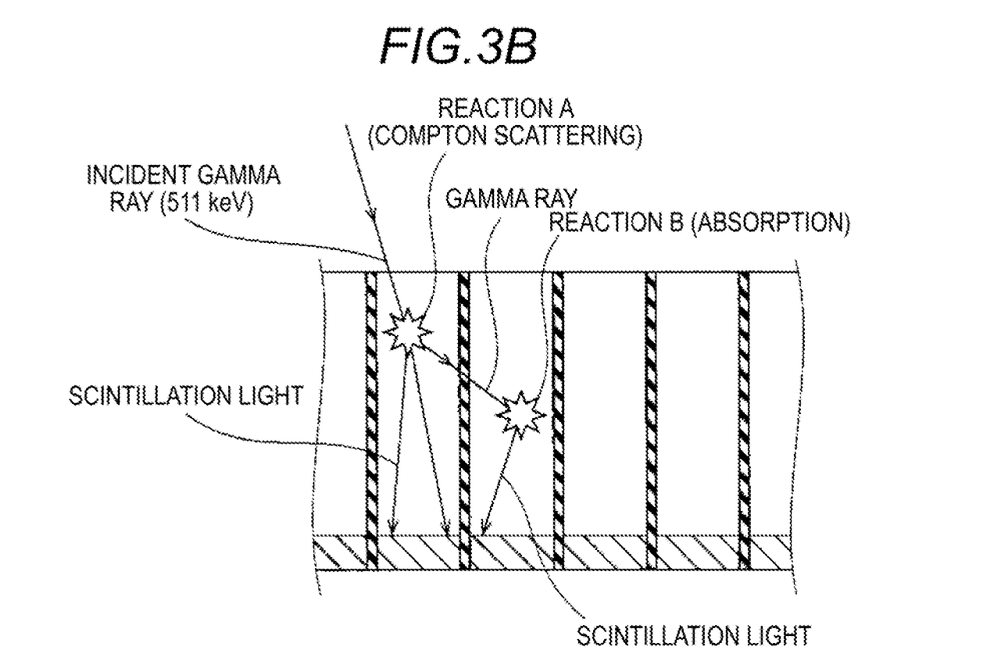
FIG. 3B is a diagram showing a state where the incident gamma rays respond to the plurality of scintillators according to one embodiment of the invention.

Meanwhile, as shown in FIG. 3B, there is a case in which the incident gamma rays respond to the plurality of scintillators 10. In a reaction A, the gamma ray incident to the scintillator 10 collides with electrons of the material inside the scintillator so that electrons rebound. Meanwhile, the gamma ray gives a part of energy to the electrons and is scattered to fly to the outside of the scintillator 10. The scattering of the gamma ray due to the rebounding of the electrons will be referred to as compton scattering. The rebounded electrons generates the scintillation light having energy equivalent to the finally given energy and returns to an original energy state. The energy given to the electrons by the compton scattering has a continuous distribution, but the upper limit value of the energy given to the electrons by the compton scattering is theoretically ⅔ of the energy of the incident gamma ray. The upper limit value corresponds to a case in which the incident gamma ray directly collides with electrons to be scattered in the direction of 180° (a direction opposite to the incidence).

Further, in FIG. 3B, since the gamma ray which is flipped by the electrons in the reaction A has high energy, the gamma ray enters into the other scintillators 10 beyond the reflection material. Then, in a reaction B, an absorption reaction occurs inside the adjacent scintillators 10 so that the scintillation light is generated. In this way, an event in which the incident gamma ray causes a reaction with the plurality of scintillator 10 and the scintillation light is detected by the plurality of optical detection units 2 will be referred to as a multiple scattering event. In addition, there is a case in which the gamma ray which flies outward due to the collision with the electrons causes a reaction inside the same scintillator 10 and is finally converted into the scintillation light corresponding to all energy (511 keV) inside the same scintillator 10. This case corresponds to the photoelectric absorption event. Further, there is a case in which the gamma ray which flies outward due to the collision with electrons flies to the outside of the scintillator 10 and the gamma ray having remaining energy given to electrons is not detected by the radiation detection device 100.

As an example of the detection signal value of the scintillation light, an example in which a measurement is performed by the radiation detection device 100 having one optical detection unit 2 connected to the element of one scintillator 10 is considered. However, the number of the photoelectric conversion elements 21 is not sufficient compared to the number of photons of the scintillation light. The measurement result is obtained as in a histogram shown in FIG. 4. A horizontal axis indicates an energy channel and a read value of the detected energy by an arbitrary unit. For that reason, a read value and a physical amount change are required to handle the energy having a physical meaning, but in the description of the embodiment, it is sufficient only when a relation with the read value is read. A vertical axis indicates a count number which represents the number of events corresponding to the energy value. Since the photoelectric absorption event frequently happens as in the example shown in FIG. 4, a peak occurs in the vicinity of a read value 57. This peak will be referred to as a photoelectric absorption peak. Meanwhile, continuous mountains due to the compton scattering are formed at the left side of the photoelectric absorption event. Since a right end of the mountain formed in the vicinity of the read value 48 corresponds to the upper limit value (⅔ of the energy of the incident gamma ray) of the energy of the compton scattering, the end is formed in a sharp edge shape. This edge will be referred to as a compton edge.

Figure 4:
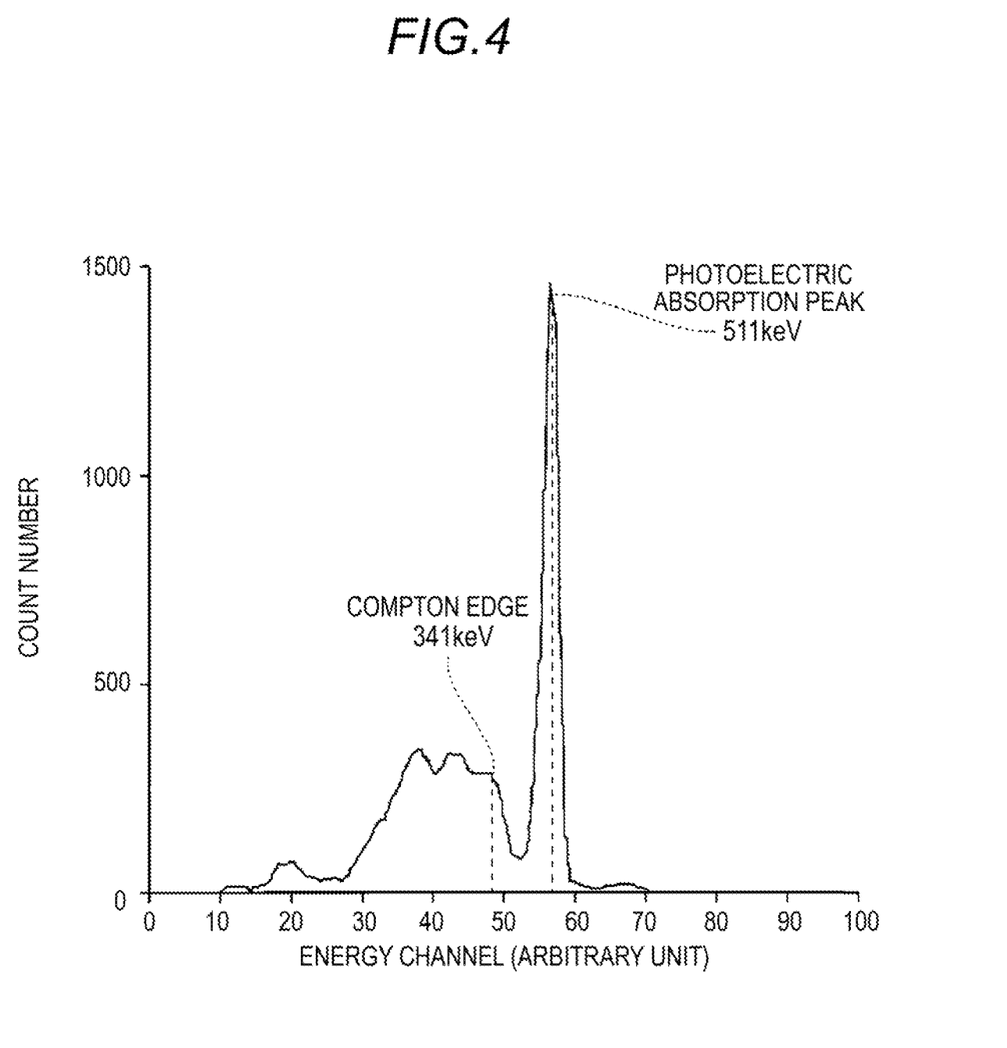
FIG. 4 is a histogram showing a detection of a gamma ray of 511 keV in a set in which one optical detection unit is connected to one scintillator of the radiation detection device according to one embodiment of the invention.

Incidentally, it is understood that the energy of the photoelectric absorption peak corresponds to 511 keV and the energy of the compton edge corresponds to 341 keV. Here, 511/341 is about 3/2=1.5. However, the detected energy channel read values are respectively about 57 and 48. 57/48 is about 1.2 and is different from the theoretically determined relation. This is caused by the detection omission according to the saturation of the photoelectric conversion element 21. In an ideal state where no detection omission occurs, 58 and 47 are larger values.

Figure 5:
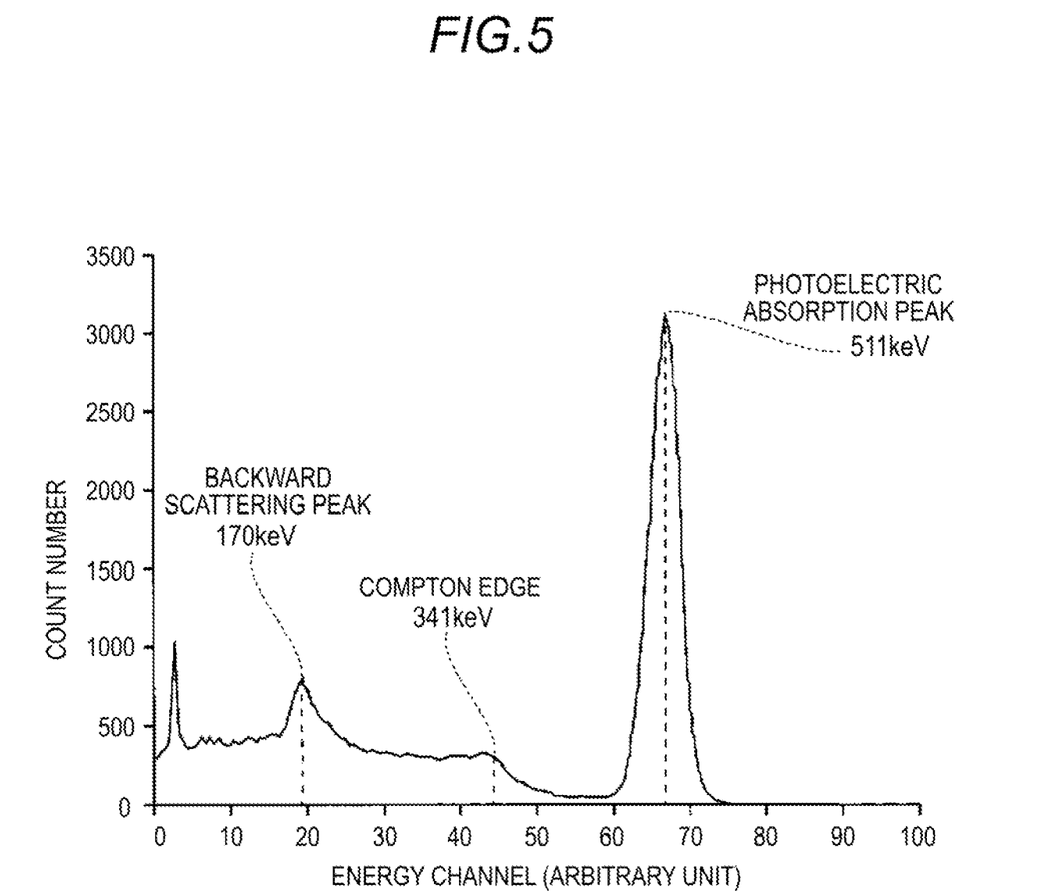
FIG. 5 is a histogram showing a detection of a gamma ray when a gamma ray of 511 keV is incident to a scintillator connected to a photomultiplier tube.

In fact, when a photomultiplier tube (PMT) which outputs a current value proportional to the scintillation light detected by the optical detection unit 2 is used, a histogram shown in FIG. 5 can be obtained. As the energy channel read value, the energy of the photoelectric absorption peak is about 67 and the compton edge is about 45. Since the photomultiplier tube outputs a signal which is proportional to the number of incident photons even when the photons are incident to the same position within a short period, 67/45 has a relation of about 1.5. In addition, the peak of the backward scattering is also a value which is theoretically determined and is ⅓ of the total energy (170 keV with respect to 511 keV).

As described above, when the linearity of the output value of the detection signal is poor, an accurate value of information necessary for the image process cannot be obtained. Thus, the shape of the histogram needs to be corrected to a shape when the linearity of the detection signal is maintained. Particularly, when the detection omission occurs due to the saturation, the full width at half maximum of the photoelectric absorption peak is narrow in appearance (an error decreases) and thus an error range cannot be accurately estimated. For this reason, there is a case in which an excessive correction or an insufficient correction occurs during the image process. Further, a value necessary for the TOF-PET apparatus is about 511 keV of the histogram. Thus, the shape of the histogram particularly in the vicinity of the photoelectric absorption peak needs to be corrected. When a correction is performed on the basis of the energy value of the photoelectric absorption peak and the energy value of the compton edge corresponding to a characteristic point near the photoelectric absorption peak, the vicinity of the photoelectric absorption peak can be effectively corrected.

Here, a quadratic function (a correlation) in which a theoretical value corresponding to the correction value is correlated with the photoelectric absorption peak read value and the compton edge read value included in the histogram is supposed. Generally, since the quadratic function is expressed by $x = ay^2 + by + c$, values of three points are required in order to determine three unknown parameters. y indicates the energy channel read value and x indicates the correction value which is continuously acquired based on the real energy. Since there is no need to consider saturation in the real energy value in which the energy channel read value corresponds to zero, the value is of course zero. Thus, since $c=0$ can be obtained by applying (0, 0), the quadratic function can be determined at one time by applying the theoretical value (the real energy value) along with the photoelectric absorption peak read value and the compton edge read value included in the histogram.

Figure 6:
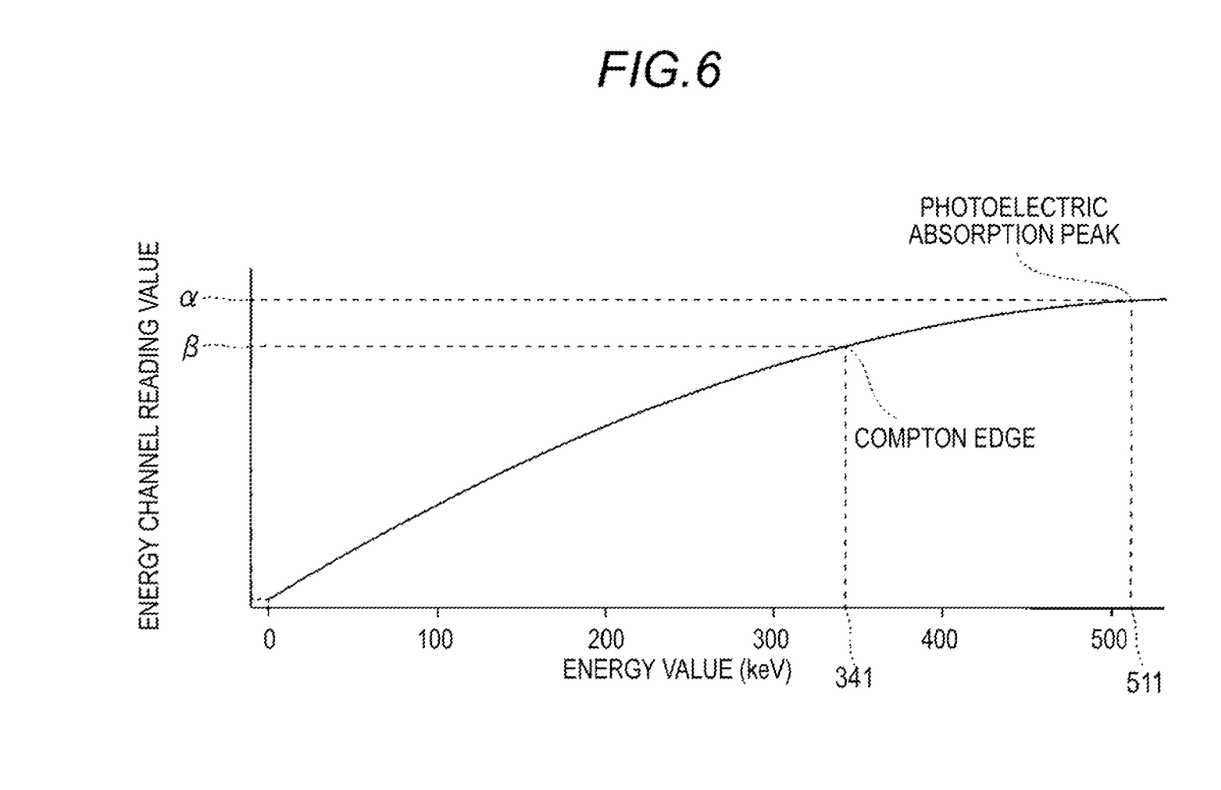
FIG. 6 is a graph of a quadratic function for correcting an output value of a detection signal according to one embodiment of the invention.

As shown in FIG. 6, a case in which a read value α of energy corresponding to the photoelectric absorption peak and a read value β of energy corresponding to the compton edge are obtained is considered. In this case, a quadratic function having a monotone increasing shape upward shown in FIG. 6 can be obtained by applying the values of two points when y=α for x=511 and y=β for x=341. Since the shape of the graph of the quadratic function protrudes upward, it shows a good approximation in which the number of the photoelectric conversion elements 21 is limited and the upper limit (the upper limit value of the detected energy) exists due to the saturation of the number of detected photons (the detection value). Accordingly, all read values (y values) can be correlated with the correction values (x values) representing the real energy value in the detection range (the range in which an approximation of the quadratic function is valid). Thus, since the shape of the quadratic function is determined, it is possible to simply and easily obtain the correlation between the read value (y value) and the correction value (x value) by the graph of the quadratic function capable of obtaining the real energy value by applying the known values of two points. Since the obtained correlation function have the same shape under the same condition, the detection signal can be corrected when the function is acquired once.

Figure 7:
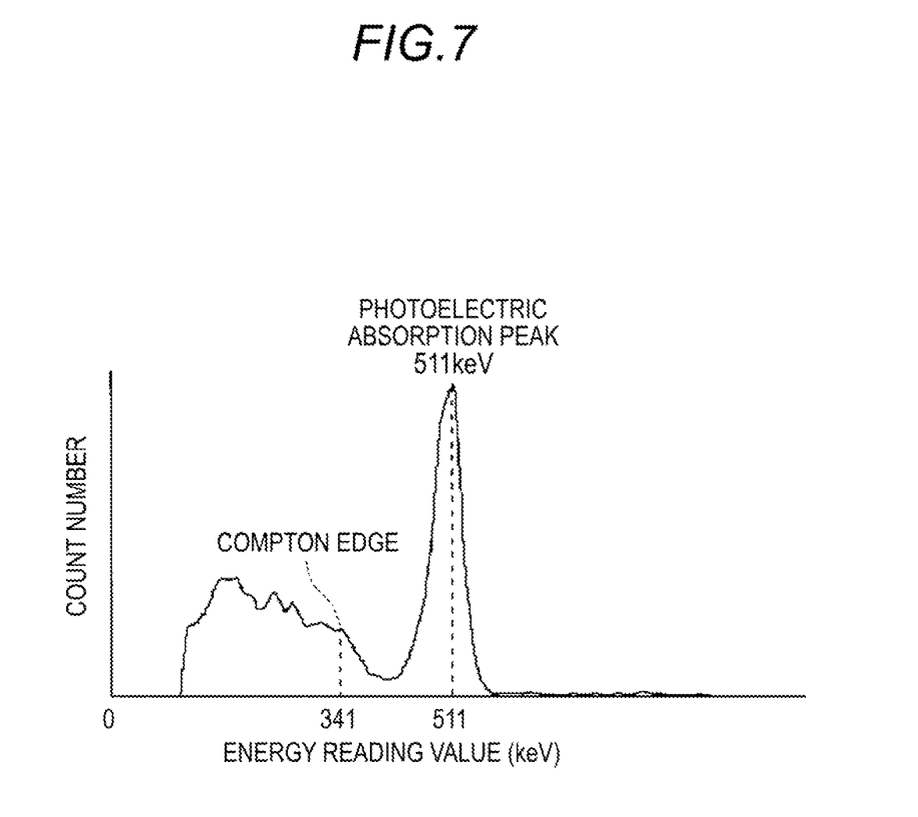
FIG. 7 is a histogram showing a correction of a detected gamma ray of 511 keV in a set in which one optical detection unit is connected to one scintillator of the radiation detection device according to one embodiment of the invention.

When a correction is performed by the correlation of the quadratic function obtained in the same way in the histogram of FIG. 4, a histogram of FIG. 7 can be obtained. From the corrected histogram, the full width at half maximum of the photoelectric absorption peak can be obtained with high accuracy. Since the detection signal of 511 keV is necessary in the TOF-PET apparatus (including the general positron emission tomography apparatus), the shape of the histogram particularly in the vicinity of 511 keV needs to be acquired with high accuracy. As described above, the detection signal of 511 keV can be appropriately corrected by the correction based on the photoelectric absorption peak in the detection of the energy of 511 keV and the compton edge corresponding to the feature in the vicinity thereof.

Figure 2A:
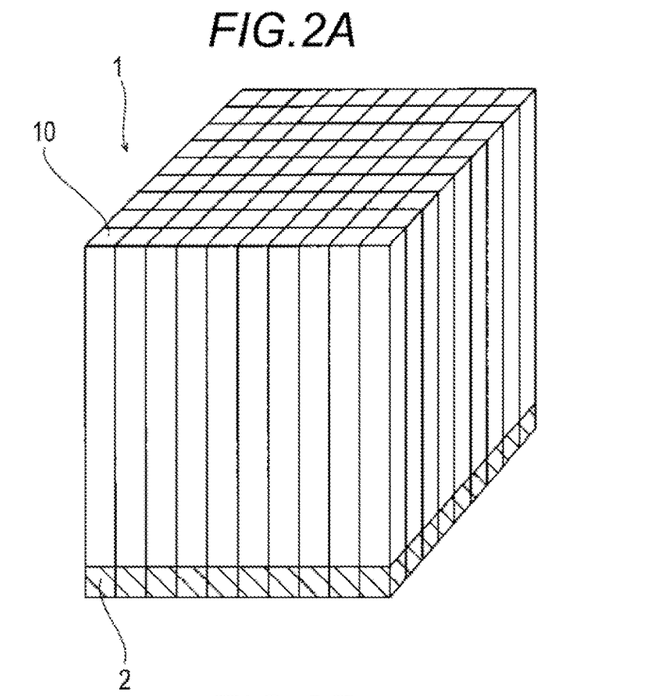
FIG. 2A is a diagram showing a scintillator group according to one embodiment of the invention.
Figure 2B:
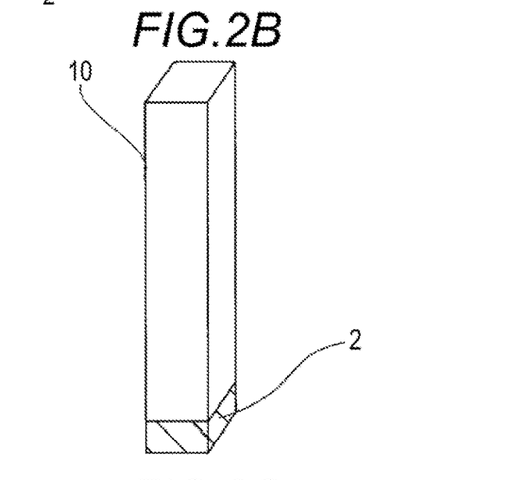
FIG. 2B is a diagram showing a scintillator according to one embodiment of the invention.
Figure 2C:
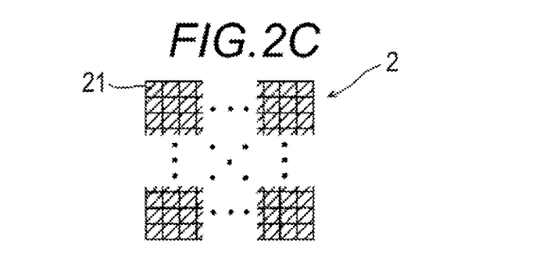
FIG. 2C is a diagram showing an optical detection unit 2 according to one embodiment of the invention.

Here, the histogram of FIG. 4 illustrates an example of a case where one scintillator 10 and one optical detection unit 2 are connected to each other, but in the real radiation detection device 100, the plurality of scintillators 10 are treated in a group as shown in FIG. 2A or 3. When the plurality of scintillators 10 are arranged closely, a correction due to a multiple scattering event needs to be also performed in addition to the detection omission caused by the saturation of photons. Here, an example will be described in which the incidence of the gamma ray having an energy value of 511 keV is measured in the radiation detection device 100 in which a set obtained by connecting one optical detection unit 2 to the element of one scintillator 10 is grouped in a matrix shape of four rows and four columns. Further, the reflection material is provided between the scintillators 10. The measurement result is obtained like a histogram shown in FIG. 8.

As in FIG. 3B, a multiple scattering event is considered in which a part of the energy of the incident gamma ray is detected by the optical detection unit 2 connected to the scintillator 10 and the remaining energy is detected by the optical detection unit 2 connected to the adjacent scintillator 10. When the scintillation light corresponding to the energy of 511 keV is detected by one optical detection unit 2, the detection omission occurs due to saturation and thus the output value of the detection signal decreases. Meanwhile, when the energy of 511 keV is distributed in the plurality of optical detection units 2 (for example, when the energy is equally detected by two optical detection units 2), the degree of the detection omission due to saturation is relatively smaller than the case where the energy is detected by one optical detection unit 2. Thus, the output value of the detection signal is not so small. In this way, the value of the detection signal to be output becomes different due to the number of the optical detection units 2 used for detection although the total energy of the gamma ray of 511 keV is detected.

Figure 8:
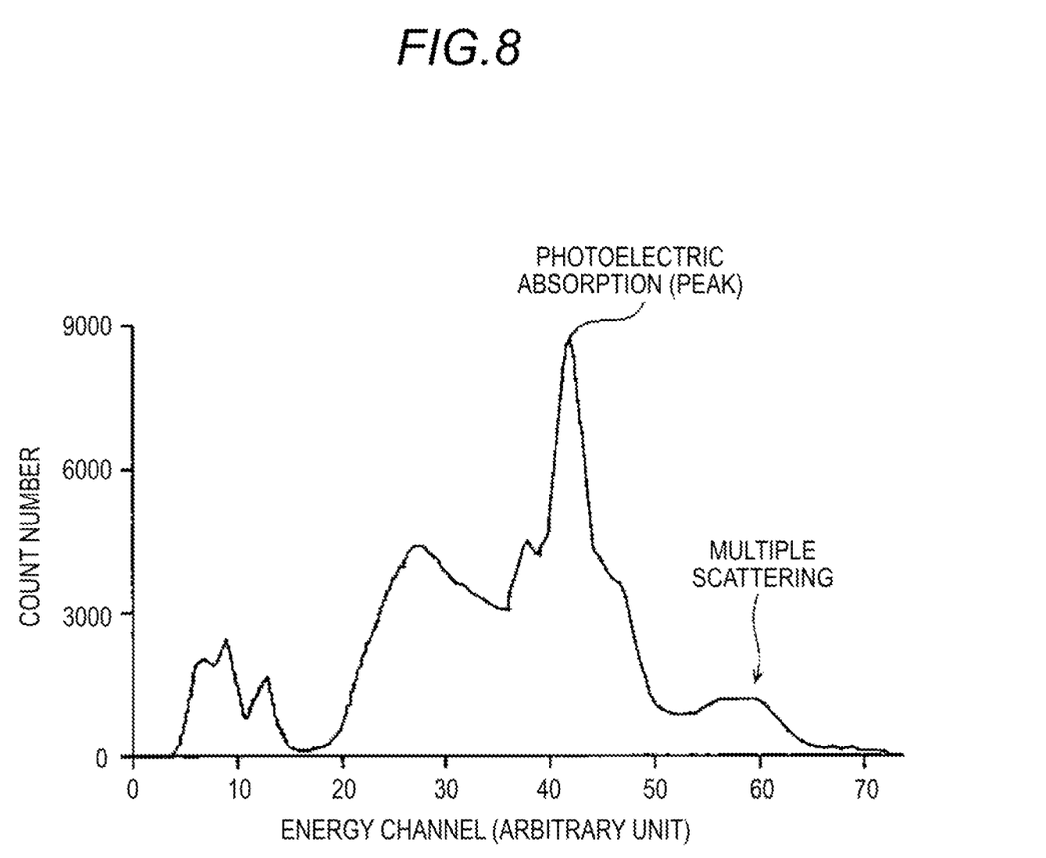
FIG. 8 is a histogram showing a detection of a gamma ray of 511 keV when a set in which one optical detection unit is connected to one scintillator of the radiation detection device according to one embodiment of the invention is grouped in a matrix shape of four rows and four columns.

For that reason, a mountain having larger energy value than the photoelectric absorption peak in appearance is caused by the multiple scattering event as shown in FIG. 8. Since the mountain of the multiple scattering event and the mountain (the peak) of the photoelectric absorption event originally correspond to the same energy (511 keV), a correction is needed. Specifically, it is possible to identify whether the position signal output from each optical detection unit 2 is a signal of the energy detected by one optical detection unit 2 or a signal of the energy detected by the plurality of optical detection units in addition to the energy detection signal of the scintillation light output from each block of the scintillator 10. Accordingly, an appropriate correction (for example, a correction of matching the energy value of the peak corresponding to the photoelectric absorption event and the energy value corresponding to the multiple scattering event) can be performed for the multiple scattering event.

Figure 9:
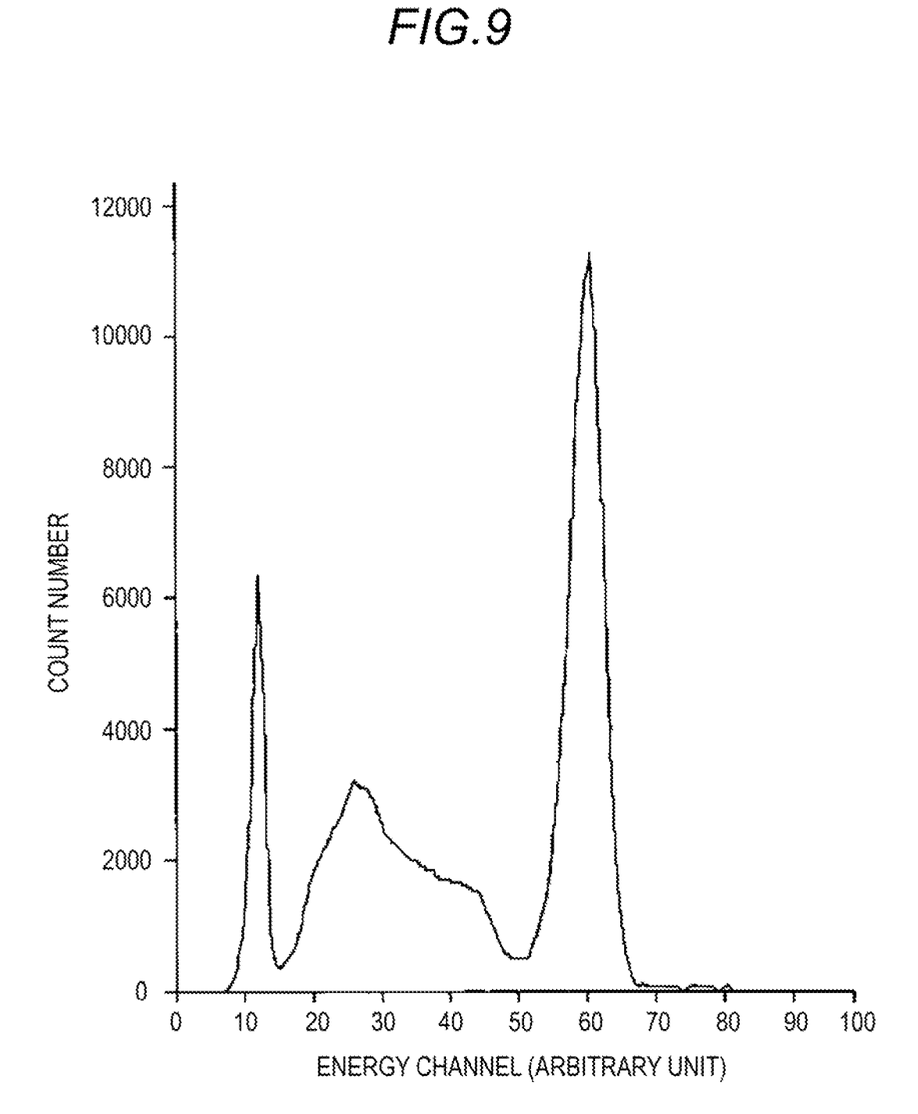
FIG. 9 is a histogram showing a correction of a detected gamma ray of 511 keV when a set in which one optical detection unit is connected to one scintillator of the radiation detection device according to one embodiment of the invention is grouped in a matrix shape of four rows and four columns.

In a histogram shown in FIG. 9, the energy signal output from each optical detection unit 2 is corrected in consideration of the number of the optical detection units 2 detected at the same time. In the histogram of FIG. 8, peaks are observed at different positions in the photoelectric absorption event and the multiple scattering event due to the number of the optical detection units 2 although they correspond to the same total energy (511 keV), but in the histogram of FIG. 9, one peak is observed at the integrated position of the photoelectric absorption event. In this way, when the influence of the multiple scattering event can be corrected, a measurement result having better linearity can be obtained by further correcting the detection omission caused by saturation.

EFFECT OF EMBODIMENT

In the embodiment, the following effect can be obtained.

In the embodiment, as described above, the scintillator group 1 which includes the plurality of scintillators 10 emitting a plurality of scintillation lights based on the receiving of the radiation having a predetermined energy amount, the plurality of optical detection units 2 which include the plurality of photoelectric conversion elements 21 emitting detection signals based on the incidence of the scintillation light, and the control unit 3 which acquires the detection signals output from the optical detection units 2 are provided. Further, the optical detection unit 2 is provided in each scintillator to detect the scintillation light generated from one scintillator. Further, the control unit 3 is configured to correct the detection signal on the basis of a plurality of features included in the histogram based on the acquired detection signal and the value of the energy of the radiation. Accordingly, since the optical detection unit 2 detects the scintillation light generated from one scintillator 10, it is possible to accurately acquire information on a certain scintillator to which the gamma ray is incident. Further, since the scintillation light is made to be incident to one optical detection unit 2, a variation in the path of the scintillation light is suppressed and thus the gamma ray incidence time can be acquired with high accuracy. Further, since the detection signal is corrected on the basis of a plurality of features included in the histogram based on the acquired detection signal and the value of the energy of the radiation, the detection omission due to the saturation can be corrected and thus the detection signal read value (the energy) can be corrected with high accuracy. As a result, it is possible to highly accurately acquire the gamma ray incidence time, the gamma ray incidence position, and the energy generated by the gamma ray. Particularly, in the case of the application to the TOF-PET apparatus 101 which acquires a position where the pair annihilation of electrons and positrons occurs on the paths of two gamma rays from a difference in detection time of two gamma rays caused by the pair annihilation of electrons and positrons, the gamma ray incidence time and the gamma ray incidence position can be acquired with high accuracy and thus a position where the pair annihilation of electrons and positrons occurs can be acquired with high accuracy.

Further, in the embodiment, as described above, the control unit 3 is configured to acquire the correlation between the detection value of the optical detection unit 2 and the correction value of the detection value for correcting the detection signals on the basis of the photoelectric absorption peak read value and the compton edge read value which are features included in the histogram. Accordingly, since the correlation between the detection value of the optical detection unit 2 and the correction value of the detection value for correcting the detection signal can be acquired only from the photoelectric absorption peak read value and the compton edge read value corresponding to the radiation having predetermined energy, information necessary for the correction can be simply and easily acquired.

Further, in the embodiment, as described above, the correlation to be acquired by the control unit 3 is acquired on the basis of the quadratic function in which the theoretical value corresponding to the correction value is correlated with the photoelectric absorption peak read value and the compton edge read value included in the histogram. Accordingly, since the correlation for correcting the read values can be determined by the quadratic function, the correlation can be acquired by a simple and easy process. Specifically, the shape of the quadratic function can be simply and easily determined by three points including an origin (in which the corrected value is zero when the read value is zero), a point representing the photoelectric absorption peak (which is the predetermined total energy of the incident gamma ray corresponding to the corrected value for the photoelectric absorption peak read value), and a point representing the compton edge (which is $2/3$ of the predetermined total energy of the incident gamma ray corresponding to the corrected value for the photoelectric absorption peak read value) and determined from the theoretical value corresponding to the read value and the correction value.

Further, in the embodiment, as described above, the control unit 3 is configured to correct the vicinity of the photoelectric absorption peak included in the histogram of the scintillation light on the basis of the acquired detection signal. Accordingly, since the shape of the photoelectric absorption peak can be accurately corrected, it is possible to highly accurately acquire the full width at half maximum representing a variation in the photoelectric absorption peak. As a result, it is possible to accurately estimate an error in calculation using the gamma ray incidence time, the gamma ray incidence position, and the energy obtained by measurement. Particularly, in the case of the application to the TOF-PET apparatus 101, an excessive correction or an insufficient correction can be suppressed when the diagnosis image formed by measurement data is corrected.

Further, in the embodiment, as described above, the radiation detection device 100 is used in the TOF-PET apparatus 101. According to such a configuration, it is possible to more accurately detect the incidence time of the gamma ray emitted by the pair annihilation of electrons and positrons.

MODIFIED EXAMPLE

In addition, the embodiment disclosed herein is merely an example and should not be considered to limit the invention. The scope of the invention is illustrated by the scope of the appended claims rather than the description of the embodiment described above, and includes all changes (modified examples) within the meaning and scope equivalent to the scope of claims.

For example, in the above-described embodiment, an example in which the peak and the compton edge of the photoelectric absorption event are used as a plurality of features for correction has been described, but the invention is not limited thereto. In the invention, the peak of the backward scattering event shown in, for example, FIG. 5 may be used as the feature. The peak of the backward scattering event is the peak of the energy corresponding to a case where the gamma ray collides with the wall surface of the detector or the subject so that a direction is turned back by 180° and the gamma ray is incident to the scintillator 10 and is theoretically a value of $1/3$ of the total energy of the gamma ray. In addition, when the quadratic function is used as the correlation for the correction, at least the energy values of three points of which true values can be obtained in advance are necessary.

Further, in the above-described embodiment, the radiation having a predetermined energy amount is the gamma ray of 511 keV generated by the pair annihilation of electrons and positrons, but the invention is not limited thereto. In the invention, the radiation may have a different energy amount.

Further, in the above-described embodiment, an example of using the quadratic function as the correlation for correction has been described, but the invention is not limited thereto. In the invention, another function may be used as the correlation for correction. For example, a polynomial expression such as a tertiary function considering a higher order term may be used by increasing the number of the features which can be compared with the read value and the given value.

In the above-described embodiment, an example of determining the function by acquiring the values of the features as many as the unknown values of the function (the quadratic function) corresponding to the correlation for correction has been described, but the invention is not limited thereto. In the invention, a function which needs to be obtained may be determined by a least-squares method based on the true value and the read value of the obtained feature. In this case, arbitrary functions may be used as the correlation instead of the elementary functions.

Further, in the above-described embodiment, an example in which the block (the unit of grouping the energy detection signal) of the scintillators included in the scintillator group 1 is a group of the scintillators 10 of nine rows and ten columns has been described, but the invention is not limited thereto. In the invention, the number of the blocks of the scintillators may be arbitrarily set as long as one optical detection unit 2 is connected to one scintillator 10. Further, a unit of grouping the scintillator 10 is not limited to a two-dimensional array and may be a one-dimensional array.

Further, in the above-described embodiment, an example in which the radiation detection device 100 is used in the TOF-PET apparatus (the TOF positron emission tomography apparatus) 101 has been described, but the invention is not limited thereto. In the invention, the radiation detection device 100 may be used in a general PET apparatus (the positron emission tomography apparatus). Further, the radiation detection device may be used in, for example, various apparatuses detecting a radiation for the purpose of non-destructive inspection or natural radiation dosimetry.

What is claimed is:

1. A radiation detection device comprising:
   a scintillator group which comprises a plurality of scintillators emitting a plurality of scintillation lights on the basis of receiving of a radiation having a predetermined energy amount;
   a plurality of optical detection units which comprise a plurality of photoelectric conversion elements outputting detection signals on the basis of incidence of the scintillation light; and
   a control unit which acquires the detection signals output from the optical detection units,
   wherein an optical detection unit in the plurality of optical detection units is provided in each scintillator and configured to detect the scintillation light generated from one scintillator, and
   wherein the control unit is configured to identify a read value of an energy of a photoelectric absorption peak and a read value of an energy of a Compton edge included in a histogram, and is further configured to correct the detection signals on the basis of the read value of the energy of the photoelectric absorption peak and the read value of the energy of the Compton edge included in a histogram based on the acquired detection signals, a theoretical value of an energy of the photoelectric absorption peak and a theoretical value of an energy of the Compton edge.

2. The radiation detection device according to claim 1, wherein the control unit is configured to acquire a correlation between a detection value output by an optical detection unit in the plurality of optical detection units and a correction value of the detection value for correcting the detection signal output by the optical detection unit based on the read value of the energy of the photoelectric absorption peak and the read value of the energy of the Compton edge which are the features included in the histogram.

3. The radiation detection device according to claim 2, wherein the control unit acquires the correlation based on a quadratic function in which a theoretical value corresponding to the correction value is correlated with the read value of the energy of the photoelectric absorption peak and the read value of the energy of the Compton edge included in the histogram.

4. The radiation detection device according to claim 2, wherein the control unit is configured to correct the vicinity of the photoelectric absorption peak included in the histogram of the scintillation light on the basis of the acquired detection signals.

5. The radiation detection device according to claim 1, wherein the radiation detection device is used in a positron emission tomography apparatus.

* * * * *